(12) United States Patent
Smith

(10) Patent No.: US 9,585,394 B2
(45) Date of Patent: *Mar. 7, 2017

(54) OPHTHALMIC CONTACT LENS SOLUTIONS CONTAINING FORMS OF VITAMIN B

(71) Applicant: FXS Ventures, LLC, Salem, NH (US)

(72) Inventor: Francis X. Smith, Salem, NH (US)

(73) Assignee: FXS VENTURES, LLC, Salem, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/055,749

(22) Filed: Feb. 29, 2016

(65) Prior Publication Data

US 2016/0174562 A1    Jun. 23, 2016

Related U.S. Application Data

(63) Continuation of application No. 13/679,605, filed on Nov. 16, 2012, now Pat. No. 9,308,264, which is a continuation-in-part of application No. 11/620,318, filed on Jan. 5, 2007, now abandoned, which is a continuation-in-part of application No. 10/544,150, filed as application No. PCT/US01/46841 on Nov. 8, 2001, now abandoned.

(60) Provisional application No. 60/246,689, filed on Nov. 8, 2000, provisional application No. 60/246,709, filed on Nov. 8, 2000, provisional application No. 60/246,708, filed on Nov. 8, 2000, provisional application No. 60/246,707, filed on Nov. 8, 2000.

(51) Int. Cl.

| | |
|---|---|
| *A01N 47/44* | (2006.01) |
| *A61K 47/18* | (2006.01) |
| *A61K 47/22* | (2006.01) |
| *A61K 47/26* | (2006.01) |
| *A61L 12/14* | (2006.01) |
| *C11D 3/00* | (2006.01) |
| *C11D 3/28* | (2006.01) |
| *C11D 3/32* | (2006.01) |
| *C11D 3/33* | (2006.01) |
| *C11D 3/34* | (2006.01) |
| *C11D 3/37* | (2006.01) |
| *C11D 3/48* | (2006.01) |
| *C11D 3/16* | (2006.01) |
| *C11D 3/20* | (2006.01) |
| *C11D 3/30* | (2006.01) |
| *C11D 3/36* | (2006.01) |
| *A01N 25/00* | (2006.01) |
| *A01N 33/12* | (2006.01) |

(52) U.S. Cl.
CPC ............. *A01N 47/44* (2013.01); *A01N 25/00* (2013.01); *A01N 33/12* (2013.01); *A61K 47/18* (2013.01); *A61K 47/22* (2013.01); *A61K 47/26* (2013.01); *A61L 12/142* (2013.01); *A61L 12/145* (2013.01); *A61L 12/147* (2013.01); *C11D 3/0078* (2013.01); *C11D 3/168* (2013.01); *C11D 3/2065* (2013.01); *C11D 3/28* (2013.01); *C11D 3/30* (2013.01); *C11D 3/32* (2013.01); *C11D 3/323* (2013.01); *C11D 3/33* (2013.01); *C11D 3/3481* (2013.01); *C11D 3/362* (2013.01); *C11D 3/37* (2013.01); *C11D 3/3703* (2013.01); *C11D 3/48* (2013.01)

(58) Field of Classification Search
CPC ....... A61K 47/22; A61K 47/26; A61L 12/142; A61L 12/145; C11D 3/0078; C11D 3/28; C11D 3/32; C11D 3/323; C11D 3/33; C11D 3/3481; C11D 3/3703; C11D 3/48; C11D 3/168; C11D 3/2065; C11D 3/30; C11D 3/362; A01N 3/0078; A01N 3/28; A01N 3/32; A01N 3/323; A01N 3/33; A01N 3/3481; A01N 3/3703; A01N 3/48; A01N 3/168; A01N 3/2065; A01N 3/30; A01N 3/362

See application file for complete search history.

(56) References Cited

U.S. PATENT DOCUMENTS

| | | |
|---|---|---|
| 1,432,345 A | 10/1922 | Lasker |
| 2,445,366 A | 7/1948 | Rigby |
| 2,976,576 A | 3/1961 | Wichterle |

(Continued)

FOREIGN PATENT DOCUMENTS

| | | |
|---|---|---|
| EP | 734732 A1 | 10/1996 |
| EP | 812592 A1 | 12/1997 |

(Continued)

OTHER PUBLICATIONS

Ballweber et al.; "In Vitro Microbicical Activities . . . " Antimicrobial Agetns and Chemotherapy, Jan. 2002; pp. 34-41; vol. 46, No. 1.

(Continued)

*Primary Examiner* — Sean Basquill
(74) *Attorney, Agent, or Firm* — Peter Mikesell; Christopher E. Blank; Schmeiser, Olsen & Watts, LLP

(57) ABSTRACT

The present invention relates to improved ophthalmic solutions that employ select B vitamins; pyridoxine and its salts; and thiamine and its salts in order to more effectively preserve solutions and to reduce the degree to which cationic preservatives will deposit on contact lenses. Ophthalmic solutions are here understood to include contact lens treatment solutions, such as cleaners, soaking solutions, conditioning solutions and lens storage solutions, as well as wetting solutions and in-eye solutions for treatment of eye conditions.

20 Claims, No Drawings

(56) References Cited

U.S. PATENT DOCUMENTS

| | | | |
|---|---|---|---|
| 3,044,937 A | 7/1962 | Krezanoski | |
| 3,428,576 A | 2/1969 | Dickinson | |
| 3,429,576 A | 2/1969 | Yoshiaki | |
| 3,503,393 A | 3/1970 | Manley | |
| 3,591,329 A | 7/1971 | Chromecek | |
| 3,689,673 A | 9/1972 | Phares | |
| 3,755,561 A | 8/1973 | Rankin | |
| 3,873,696 A | 3/1975 | Randeri | |
| 3,876,768 A | 4/1975 | Blank | |
| 3,888,782 A | 6/1975 | Boghosian | |
| 3,910,296 A | 10/1975 | Karageozian | |
| 3,911,107 A | 10/1975 | Krezanoski | |
| 3,912,450 A | 10/1975 | Boucher | |
| 3,943,251 A | 3/1976 | Medow | |
| 4,022,834 A | 5/1977 | Gundersen | |
| 4,029,817 A | 6/1977 | Blanco | |
| 4,046,706 A | 9/1977 | Krezanoski | |
| 4,136,173 A | 1/1979 | Pramoda | |
| 4,136,175 A | 1/1979 | Rideout | |
| 4,136,534 A | 1/1979 | Villa | |
| 4,209,817 A | 6/1980 | McGinnis | |
| 4,354,952 A | 10/1982 | Riedhammer | |
| 4,361,458 A | 11/1982 | Grajek | |
| 4,361,548 A | 11/1982 | Smith | |
| 4,361,549 A | 11/1982 | Kung | |
| 4,394,381 A | 7/1983 | Sherrill | |
| 4,409,205 A * | 10/1983 | Shively | A61K 9/0048 424/78.04 |
| 4,439,417 A | 3/1984 | Matsunaga | |
| 4,525,346 A | 6/1985 | Stark | |
| 4,537,746 A * | 8/1985 | Ogunbiyi | A01N 47/44 422/28 |
| 4,599,360 A | 7/1986 | Fukami | |
| RE32,672 E | 5/1988 | Huth | |
| 4,748,189 A | 5/1988 | Su | |
| 4,758,595 A | 7/1988 | Ogunbiyi | |
| 4,783,488 A | 11/1988 | Ogunbiyi | |
| 4,804,454 A | 2/1989 | Asakura | |
| 4,820,352 A | 4/1989 | Riedhammer | |
| 4,826,879 A | 5/1989 | Yamamoto | |
| 4,836,986 A | 6/1989 | Ogunbiyi | |
| 4,863,900 A | 9/1989 | Pollock | |
| 4,891,423 A | 1/1990 | Stockel | |
| 4,988,710 A | 1/1991 | Olney | |
| 4,997,626 A | 3/1991 | Dziabo | |
| 5,030,721 A | 7/1991 | Kasai | |
| 5,078,908 A | 1/1992 | Ripley | |
| 5,089,261 A | 2/1992 | Nitecki | |
| 5,122,354 A | 6/1992 | Tsuji | |
| 5,174,872 A | 12/1992 | Scott | |
| 5,175,161 A | 12/1992 | Yokoyama | |
| 5,182,258 A | 1/1993 | Chiou | |
| 5,192,535 A | 3/1993 | Davis | |
| 5,279,673 A | 1/1994 | Dziabo | |
| 5,300,296 A | 4/1994 | Holly | |
| 5,306,440 A | 4/1994 | Ripley | |
| 5,361,287 A | 11/1994 | Williamson | |
| 5,380,303 A | 1/1995 | Holly | |
| 5,439,572 A | 8/1995 | Pankow | |
| 5,449,658 A | 9/1995 | Unhoch | |
| 5,460,808 A | 10/1995 | Mausner | |
| 5,494,937 A | 2/1996 | Asgharian | |
| 5,547,990 A | 8/1996 | Hall | |
| 5,591,426 A * | 1/1997 | Dabrowski | A61K 9/0048 424/78.04 |
| 5,591,773 A | 1/1997 | Grunberger | |
| 5,607,681 A | 3/1997 | Galley | |
| 5,624,958 A | 4/1997 | Isaacs | |
| 5,661,130 A | 8/1997 | Meezan | |
| 5,674,450 A | 10/1997 | Lin | |
| 5,691,379 A | 11/1997 | Ulrich | |
| 5,718,895 A | 2/1998 | Asgharian | |
| 5,719,110 A | 2/1998 | Cook | |
| 5,741,817 A | 4/1998 | Chowhan | |
| 5,770,582 A | 6/1998 | von Borstel | |
| 5,780,450 A | 7/1998 | Shade | |
| 5,807,585 A | 9/1998 | Martin | |
| 5,811,446 A | 9/1998 | Thomas | |
| 5,817,277 A | 10/1998 | Mowrey McKee | |
| 5,854,303 A | 12/1998 | Powell | |
| 5,869,468 A | 2/1999 | Freeman | |
| 5,888,950 A | 3/1999 | Potini | |
| 5,891,733 A | 4/1999 | Inoue | |
| 5,925,317 A | 7/1999 | Rogalskyj | |
| 5,925,320 A | 7/1999 | Jones | |
| 5,925,371 A | 7/1999 | Ishiwatari | |
| 5,942,218 A | 8/1999 | Kirschner | |
| 5,945,446 A | 8/1999 | Laub | |
| 5,965,736 A | 10/1999 | Akhavan Tafti | |
| 5,968,904 A | 10/1999 | Julian | |
| 6,001,805 A | 12/1999 | Jaynes | |
| 6,008,195 A | 12/1999 | Selsted | |
| 6,022,732 A | 2/2000 | Bakhit | |
| 6,024,954 A | 2/2000 | Park | |
| 6,056,920 A | 5/2000 | Lepre | |
| 6,117,869 A | 9/2000 | Picard | |
| 6,121,327 A | 9/2000 | Tsuzuki | |
| 6,126,706 A | 10/2000 | Matsumoto | |
| 6,139,646 A | 10/2000 | Asgharian | |
| 6,143,244 A * | 11/2000 | Xia | A61L 12/141 134/26 |
| 6,153,568 A | 11/2000 | McCanna | |
| 6,162,393 A | 12/2000 | De Bruiju | |
| 6,191,110 B1 | 2/2001 | Jaynes | |
| 6,309,596 B1 | 10/2001 | Xia | |
| 6,309,658 B1 | 10/2001 | Xia | |
| 6,432,983 B1 | 8/2002 | Cullinan | |
| 6,456,563 B1 | 9/2002 | Kajimoto | |
| 6,550,862 B2 | 4/2003 | Kain | |
| 6,617,291 B1 | 9/2003 | Smith | |
| 6,624,203 B1 | 9/2003 | Smith | |
| 9,308,264 B2 * | 4/2016 | Smith | A61K 47/18 |
| 2002/0155961 A1 | 10/2002 | Schwind | |
| 2003/0190258 A1 | 10/2003 | Smith | |
| 2005/0042198 A1 | 2/2005 | Smith | |
| 2006/0142169 A1 | 6/2006 | Smith | |
| 2006/0148665 A1 | 7/2006 | Smith | |
| 2007/0104744 A1 | 5/2007 | Smith | |

FOREIGN PATENT DOCUMENTS

| | | | |
|---|---|---|---|
| EP | 0923950 | 6/1999 | |
| EP | 1323426 | 7/2003 | |
| GB | 1398058 A | 6/1975 | |
| GB | 1431841 A | 4/1976 | |
| JP | 58010517 A | 1/1983 | |
| JP | 05-017355 | * 1/1993 | A61K 31/44 |
| JP | 05017355 | 1/1993 | |
| JP | 8104636 A | 4/1996 | |
| JP | 10108899 A | 4/1998 | |
| JP | 11199899 | 7/1999 | |
| JP | 2000016965 A | 1/2000 | |
| JP | 2001302518 | 10/2001 | |
| JP | 2002104971 | 4/2002 | |
| JP | 2006089403 A | 4/2006 | |
| JP | 2006206565 | 8/2006 | |
| JP | 2008152584 A | 7/2008 | |
| RU | 1803110 A1 | 7/1990 | |
| RU | 2127100 C1 | 3/1999 | |
| WO | WO9101763 | 2/1991 | |
| WO | WO9204905 A1 | 4/1992 | |
| WO | WO9211876 A1 | 7/1992 | |
| WO | WO9221049 A1 | 11/1992 | |
| WO | WO9304706 A1 | 3/1993 | |
| WO | WO9400160 A1 | 1/1994 | |
| WO | WO9500176 A1 | 1/1995 | |
| WO | WO9606603 A1 | 3/1996 | |
| WO | WO9734834 A1 | 9/1997 | |
| WO | WO9741215 A1 | 11/1997 | |
| WO | WO9923887 A1 | 5/1999 | |
| WO | WO9937295 A1 | 7/1999 | |
| WO | WO0007634 A1 | 2/2000 | |
| WO | WO0011514 A1 | 3/2000 | |
| WO | WO0238161 A2 | 5/2002 | |

(56) References Cited

FOREIGN PATENT DOCUMENTS

| WO | WO02055118 | 7/2002 |
|----|------------|--------|
| WO | WO02060495 | 8/2002 |
| WO | WO02062260 A2 | 8/2002 |
| WO | WO2004024855 | 3/2004 |
| WO | WO2004054629 | 7/2004 |
| WO | WO2008077110 A2 | 6/2008 |

OTHER PUBLICATIONS

Creighton, Thomas; "Proteins Structures and Molecular Properties", W.H. Freeman & col, NY, 1994, pp. 179-182.

De Luccca "Fungicidal Properties, Sterol Binding . . . " Can. J. of Micrbiology, Jun. 1998, pp. 514-520, vol. 44, No. 6.

Goebbels, Martin; "Efficacy of Dexpanthenol-containing artificial tears . . . "; Klinische Monatsblaetter Fuer, Augenheilkunde, vol. 29, No. 2-3, 1996, pp. 84-88.

Keay, L. et al.; "Differentiation of Alkaline Proteases" Biochemical and Biophysical Research Comm. 1969, pp. 600-604, vol. 34, No. 5.

Keay, L. et al.; "Proteases of the Genus Bacillus II" Biotechnology & Bioengineering, Mar. 1970; pp. 213-249.

Moore, John A et al. "An assessment of Boric Acid and Borax . . . "; Reproductive Toxicol, 123, 128 (1997).

Schutte, L. et al. "The Substitution Reaction of Histidine and Some Other Imidazole Derivatives with Iodone" Tetrahedron, Supp. No. 7, 1965, pp. 295-306.

Search report dated Aug. 2, 2002 in PCT/US01/46841.

Search report dated Jun. 29, 2009 in PCT/US2008/050375.

Search report dated Oct. 17, 2008 for EP08014693.

Search report dated Dec. 6, 2005 for EP01999161.

Translation of RU2121825, Nov. 20, 1998.

Yanovskaya et al, "Effect of Low-Dose Emoxypine . . . " Bulletin of Experimental Biology and Medicine, vol. 115, No. 5, pp. 517-520, 1993.

Derwent; Pyrotonik ocular drops; XP002329199; 1999.

European Search Report in EP12007769.8 dated Jan. 30, 2013.

Martin Gobbets & Dorthea Gross; Klinische Studie zur Wirksamkeit eines dexpanthenoihaltigen Tranenersatzmittels (Siccaprotect) bei der Behandlung Trockener Augen (1996).

\* cited by examiner

OPHTHALMIC CONTACT LENS SOLUTIONS CONTAINING FORMS OF VITAMIN B

CROSS-REFERENCE TO RELATED APPLICATIONS

This application is continuation of U.S. patent application Ser. No. 13/679,605 (filed Nov. 16, 2012) which is a continuation-in-part of U.S. patent application Ser. No. 11/620,318 (filed Jan. 5, 2007) which is a continuation-in-part of U.S. patent application Ser. No. 10/544,150 (filed Aug. 1, 2005), which is a national stage entry of PCT/US01/46841 (filed Nov. 8, 2001) which claims the benefit of U.S. Provisional Patent Applications 60/246,689 (filed Nov. 8, 2000) 60/246,707 (filed Nov. 8, 2000) 60/246,708 (filed Nov. 8, 2000) and 60/246,709 (filed Nov. 8, 2000). The contents of the aforementioned applications are hereby incorporated by reference.

BACKGROUND OF THE INVENTION

The present invention relates to the field of ophthalmic solutions and their uses. In particular the invention relates to contact lens cleaning solutions, contact lens rinsing and storing solutions, solution to deliver active pharmaceutical agents to the eye, solutions for disinfecting ophthalmic devices and the like.

The present invention relates to the field of ophthalmic solutions and especially to the aspects of preservative efficacy and comfort after prolonged use. These ophthalmic solutions have been used for some period of time and are available as over the counter products. Solutions that are used in direct contact with corneal tissue such as the delivery of active pharmaceutical agent to the eye, or indirectly, such as the cleaning, conditioning or storage of devices that will come in contact with corneal tissue, such as contact lenses, there is a need to insure that these solution do not introduce sources of bacterial or other microbial infection. Thus preservatives are included to reduce the viability of microbes in the solution and to lessen the chance of contamination of the solution by the user since many of the solutions are bought, opened, used, sealed and then reused.

State of the art preservative agents include polyhexamethylene biguanide (PHMB), POLYQUAD™, chlorhexidine, and benzalkonium chloride, and the like, all of which at some concentration irritate corneal tissue and lead to user discomfort. Therefore, a solution that employs a given amount of a preservative agent, but which is made more effective by addition of an agent that is not a preservative agent would be desired.

BRIEF DESCRIPTION OF THE INVENTION

The present invention relates to improved ophthalmic solutions that employ select B vitamins; pyridoxine and its salts; and thiamine and its salts in order to more effectively preserve solutions and to reduce the degree to which cationic preservatives will deposit on contact lenses. Ophthalmic solutions are here understood to include contact lens treatment solutions, such as cleaners, soaking solutions, conditioning solutions and lens storage solutions, as well as wetting solutions and in-eye solutions for treatment of eye conditions.

DETAILED DESCRIPTION OF THE INVENTION

The solutions specifically described herein have 0.001 to about 10.0 weight percent of select B vitamins; pyridoxine and its salts; and thiamine and its salts in combination with other active ingredients useful in ophthalmic solutions such as tonicity agent, buffers, preservatives, surfactants, and antimicrobial agents.

The B family of vitamins includes thiamine (B1), riboflavin (B2), niacin (B3), dexpanthenol, panthenol, pantothenic acid (B5), pyridoxine (B6), and cobalamin (B12). While each form of B vitamin is chemically distinct, they are often found in the same nutritional sources and hence deficiency in one is often related to deficiency in the other forms. Metabolically, they work with one another to bolster metabolism, enhance immune and nervous system function, maintain healthy skin and muscle tone, and promote cell growth and division. They may also relieve stress, depression, and cardiovascular disease. A deficiency in one B vitamin often means that intake of all B vitamins is low which is why B vitamins as a nutritional source are often provided in multivitamin or B-complex formulae.

Niacin contributes to a great number of bodily processes. Among other things niacin helps convert food into energy, build red blood cells, synthesize hormones, fatty-acids and steroids. The body uses niacin in the process of releasing energy from carbohydrates. Niacin is also needed to form fat from carbohydrates and to process alcohol. Niacin also helps regulate cholesterol.

Pyridoxine is needed to make serotonin, melatonin, and dopamine. Vitamin B-6 is an essential nutrient in the regulation of mental processes and possibly assists in mood and many other health concerns Cobalamin is needed for normal nerve cell activity. Vitamin B-12 is also needed for DNA replication, and production of the mood-affecting substance called SAMe (S-adenosyl-L-methionine). Vitamin B-12 works with folic acid to control homocysteine levels. An excess of homocysteine, which is an amino acid (protein building block), may increase the risk of heart disease, stroke, and perhaps osteoporosis and Alzheimer's disease.

Other compounds such as folic acid or folate are active in combination with the B vitamins and are needed to synthesize DNA. DNA allows cells to replicate normally. Folic acid is especially important for the cells of a fetus when a woman is pregnant. Folic Acid is also needed to make SAMe and keep homocysteine levels in the blood from rising. Folic Acid (pteroylglutamic acid) is not active as such in the mammalian organism, but rather is enzymatically reduced to tetrahydrofolic acid (THFA), the coenzyme form. An interrelationship exists with vitamin B12 and folate metabolism that further involves vitamin B6: folate coenzymes participate in a large number of metabolic reactions in which there is a transfer of a one-carbon unit.

Pantothenic Acid, also sometimes referred to as coenzyme A, is the physiologically active form of pantothenic acid, and serves a vital role in metabolism as a coenzyme for a variety of enzyme-catalyzed reactions involving transfer of acetyl (two-carbon) groups. Surprisingly, pantothenic acid is essential for the growth of various microorganisms, including many strains of pathogenic bacteria.

In the form of contact lens rinsing solutions and/or pharmaceutical agent delivery system the solutions will contain, in addition to the lens or the pharmaceutical agent 0.00001 to about 10.0 weight percent of one of the vitamin B forms or a vitamin B co-metabolite chosen from the group including, but not limited to, thiamine (B1), riboflavin (B2), niacin (B3), dexpanthenol, panthenol, pantothenic acid (B5), pyridoxine (B6), and cobalamin (B12); and at least 0.00001 weight percent of a preservative.

The preservatives that are specifically useful are cationic preservatives such as polyhexamethylene biguanide (phmb), POLYQUAD™, chlorhexidine, and benzalkonium chloride, as well as other cationic preservatives that may prove useful in the present invention as well. The cationic preservatives are used at effective amounts as preservatives, and in the instance of PHMB from 0.0001 percent by weight to higher levels of about 0.01 weight percent.

The formulations may also include buffers such as phosphates, bicarbonate, citrate, borate, ACES, BES, BICINE, BIS-Tris Propane, HEPES, HEPPS, imidazole, MES, MOPS, PIPES, TAPS, TES, TRIS and Tricine.

Surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold by BASF under the trademark Cremophor.

The solutions of the present invention may contain other additives including but not limited to buffers, tonicity agents, demulcents, wetting agents, preservatives, sequestering agents (chelating agents), surface active agents, and enzymes. In one embodiment between about 0.01% and 5.0% of a simple saccharide is present. Examples of simple saccharides include mannitol; sorbitol; sucrose; dextrose and glycerin.

Other aspects include adding to the solution from 0.001 to 1 weight percent chelating agent (preferably disodium EDTA) and/or additional microbicide, (preferably 0.00001 to 0.1) weight percent polyhexamethylene biquanide (PHMB), N-alkyl-2-pyrrolidone, chlorhexidine, polyquaternium-1, hexetidine, bronopol, alexidine, low concentrations of hydrogen peroxide, and ophthalmologically acceptable salts thereof.

Ophthalmologically acceptable chelating agents useful in the present invention include amino carboxylic acid compounds or water-soluble salts thereof, including ethylenediaminetetraacetic acid, nitrilotriacetic acid, diethylenetriamine pentaacetic acid, hydroxyethylethylenediaminetriacetic acid, 1,2-diaminocyclohexanetetraacetic acid, ethylene glycol bis (beta-aminoethyl ether) in N,N,N',N' tetraacetic acid (EGTA), iminodiacetic acid and hydroxyethylamino diacetic acid. These acids can be used in the form of their water soluble salts, particularly their alkali metal salts. Especially preferred chelating agents are the di-, tri- and tetra-sodium salts of ethylenediaminetetraacetic acid (EDTA), most preferably disodium EDTA (Disodium Edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphates, tetraphosphates, trimetaphosphates, tetrametaphosphates, as well as more highly condensed phosphates in the form of the neutral or acidic alkali metal salts such as the sodium and potassium salts as well as the ammonium salt.

The pH of the solutions should be adjusted to be compatible with the eye and the contact lens, such as between 6.0 to 8.0, preferably between 6.8 to 7.8 or between 7.0 to 7.6. Significant deviations from neutral (pH 7.3) will cause changes in the physical parameters (i.e. diameter) in some contact lenses. Low pH (pH less than 5.5) can cause burning and stinging of the eyes, while very low or very high pH (less than 3.0 or greater than 10) can cause ocular damage.

The additional preservatives employed in the present invention are known, such as polyhexamethylene biguanide, N-alkyl-2-pyrrolidone, chlorhexidine, polyhexamethylenebiguanide, alexidine, polyquaternium-1, hexetidine, bronopol and a very low concentration of hydrogen peroxide, e.g., 30 to 200 ppm.

The solutions of the invention are compatible with both rigid gas permeable and hydrophilic contact lenses during storage, cleaning, wetting, soaking, rinsing and disinfection.

A typical aqueous solution of the present invention may contain additional ingredients which would not affect the basic and novel characteristics of the active ingredients described earlier, such as tonicity agents, surfactants and viscosity inducing agents, which may aid in either the lens cleaning or in providing lubrication to the eye. Suitable tonicity agents include sodium chloride, potassium chloride, glycerol or mixtures thereof the tonicity of the solution is typically adjusted to approximately 240-310 milliosmoles per kilogram solution (mOsm/kg) to render the solution compatible with ocular tissue and with hydrophilic contact lenses. In one embodiment, the solution contains 0.01 to 0.2 weight percent sodium chloride. The important factor is to keep the concentrations of such additives to a degree no greater than that would supply a chloride concentration of no greater than about 0.2 mole percent.

Suitable viscosity inducing agents can include lecithin or the cellulose derivatives such as hydroxyethylcellulose, hydroxypropylmethylcellulose and methylcellulose in amounts similar to those for surfactants, above.

Example 1

Formulations containing Pyridoxine HCl (Spectrum) and Thiamine HCl (Fisher) were prepared in a 0.2% phosphate buffer. The solutions were made isotonic with sodium chloride and preserved with polyhexamethylene biguanide at 0.0001%. The pH was adjusted to 7.2 with either 1 N sodium hydroxide or 1 N hydrochloric acid. The in vitro microbicidal activity of the solutions was determined by exposing *C. albicans* to 10 ml of each solution at room temperature for 4 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

| Additive | 4 Hour Log Reduction |
|---|---|
| Pyridoxine HCl (0.5%) | 2.0 |
| Thiamine HCl (0.5%) | 1.0 |
| Buffer Control | 0.8 |

The solution containing pyridoxine HCl and thiamine HCl showed an improvement in the activity against *C. albicans* as compared to the buffer control.

Example 2

Formulations containing dexpanthenol were prepared in a 0.25% Bis-Tris Propane buffer. The solutions were made isotonic with sodium chloride and preserved with polyhexamethylene biguanide at 0.00005%. The pH was adjusted to 7.2 with either 1 N sodium hydroxide or 1 N hydrochloric acid. The in vitro microbicidal activity of the solutions was determined by exposing *C. albicans* to 10 ml of each solution at room temperature for 4 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

| Buffer | Additive | Preservative | Dexpanthenol | Log Reduction Calibicans 4 hour |
|---|---|---|---|---|
| Bis-Tris Propane 0.25% | Cremophor 0.20% Inositol 3.0% Allantoin 0.1% | PHMB 0.5 ppm | None | 3.8 |
| Bis-Tris Propane 0.25% | Cremophor 0.20% Inositol 3.0% Allantoin 0.1% | PHMB 0.5 ppm | Dexpanthenol 0.1% | 4.9 |

This data shows that the dexpanthenol has improved preservative efficacy over a solution with a preservative alone.

Example 3

Formulations containing Dexpanthanol (Spectrum), Pyridoxine HCl (Spectrum) Thiamine HCl (Spectrum), and no Vitamin B control were prepared in a 0.5% Tris buffer containing 0.6% sodium chloride. The pH was adjusted with 1 N HCl to a final pH of 7.2. Polyhexamethylene biquanide (PHMB) at 0.0001% was added to each formulation. The in vitro anti-microbial activity of the solutions was determined by exposing E. coli to 10 ml of each solution at room temperature for 1 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

| Solution | | | Log Reduction at 1 hr |
|---|---|---|---|
| 0.5% Dexpanthenol | 0.5% Tris | 1 ppm PHMB | 4.82 |
| 0.5% Pyridoxine HCl | 0.5% Tris | 1 ppm PHMB | 4.34 |
| 0.5% Thiamine HCl | 0.5% Tris | 1 ppm PHMB | 5.12 |
| None | 0.5% Tris | 1 ppm PHMB | 0.42 |

The results showed an enhancement of the preservative in the presence of the Dexpanthanol, Pyridoxine, and Thiamine.

Example 4

Formulations containing Dexpanthanol (Spectrum), Pyridoxine HCl (Spectrum) Thiamine HCl (Spectrum), and no Vitamin B control were prepared in a 0.5% Tris buffer containing 0.6% sodium chloride. The pH was adjusted with 1 N HCl to a final pH of 7.2. Benzalkonium Chloride (BAK) at 0.0025% was added to each formulation. The in vitro anti-microbial activity of the solutions was determined by exposing E. coli to 10 ml of each solution at room temperature for 1 hour. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

| Solution | | | Log Reduction at 1 hr |
|---|---|---|---|
| 0.5% Dexpanthenol | 0.5% Tris | 25 PPM BAK | >5.12 |
| 0.5% Pyridoxine HCl | 0.5% Tris | 25 PPM BAK | >5.12 |
| 0.5% Thiamine HCl | 0.5% Tris | 25 PPM BAK | 3.30 |
| None | 0.5% Tris | 1 ppm PHMB | 0.42 |

The results showed an enhancement of the preservative in the presence of the Dexpanthanol and Pyridoxine.

What is claimed is:

1. A contact lens solution comprising:
   at least 0.00001 weight percent of polyhexamethylene biguanide;
   between 0.00001 and 10 weight percent of a panthenol that functions as a preservative enhancer;
   wherein the contact lens solution has a low chloride concentration of less than 0.1 mole percent chloride, and the combination of the polyhexamethylene biguanide, the panthenol, and the low chloride concentration provide an enhanced preservative effect relative to a corresponding contact lens solution having a chloride concentration of more than 0.2 mole percent.

2. The contact lens solution of claim 1, wherein the polyhexamethylene biguanide is present in a concentration between 0.1 parts per million and 10,000 parts per million.

3. The contact lens solution of claim 1, further comprising a physiologically compatible buffer selected from the group consisting of phosphate, bicarbonate, citrate, borate, ACES, BES, BICINE, BIS, BIS-Tris, BIS-Tris Propane, HEPES, HEPPS, imidazole, MES, MOPS, PIPES, TRIS, TAPS, TES, an amino acid, and Tricine.

4. The contact lens solution of claim 1 further comprising a wetting agent selected from the group consisting of a polysorbate surfactant, a polyoxyethylene surfactant, a phosphonates, a saponin, a polyethyoxylated glyceride, and a polyethoxylated castor oil.

5. The contact lens solution of claim 1 further comprising a polyethoxylated castor oil.

6. The contact lens solution of claim 1, further comprising between 0.01% and 5.0% of at least one simple saccharide selected from the group consisting of mannitol; sorbitol; sucrose; dextrose, glycerin and combinations thereof.

7. The contact lens solution of claim 1, further comprising between 0.001% and 1% of a chelating agent selected from the group consisting of ethylenediaminetetraacetic acid or a salt thereof, citric acid or a salt thereof, an amino carboxylic acid or a salt thereof, nitrilotriacetic acid or a salt thereof, diethylene triamine pentaacetic acid or a salt thereof, hydroxyethylethylenediaminetriacetic acid or a salt thereof, 1,2-diaminocyclohexanetetraacetic acid or a salt thereof, ethylene glycol bis (beta-aminoethyl ether)-N,N,N',N' tetraacetic acid (EGTA) or a salt thereof, iminodiacetic acid or a salt thereof, hydroxyethylamino diacetic acid or a salt thereof and a polyphosphate salt.

8. The contact lens solution of claim 1, further comprising between 0.001% and 1% of ethylenediaminetetraacetic acid or a salt thereof.

9. The contact lens solution of claim 1, further comprising between 0.00001% and 0.1% of a microbicide selected from the group consisting of N-alkyl-2-pyrrolidone, chlorhexidine, polyquaternium-1, hexetidine, bronopol, alexidine, hydrogen peroxide, and salts thereof.

10. The contact lens of claim 1, wherein the panthenol is pantothenic acid (B5) or a salt of pantothenic acid.

11. A contact lens solution comprising:
at least 0.00001 weight percent of polyquaternium-1;
between 0.00001 and 10 weight percent of a panthenol that functions as a preservative enhancer;
wherein the contact lens solution has a low chloride concentration of less than 0.1 mole percent chloride, and the combination of the polyquaternium-1, the panthenol, and the low chloride concentration provide an enhanced preservative effect relative to a corresponding contact lens solution having a chloride concentration of more than 0.2 mole percent.

12. The contact lens solution of claim 11, wherein the polyquaternium-1 is present in a concentration between 0.1 parts per million and 10,000 parts per million.

13. The contact lens solution of claim 11, further comprising a physiologically compatible buffer selected from the group consisting of phosphate, bicarbonate, citrate, borate, ACES, BES, BICINE, BIS, BIS-Tris, BIS-Tris Propane, HEPES, HEPPS, imidazole, MES, MOPS, PIPES, TRIS, TAPS, TES, an amino acid, and Tricine.

14. The contact lens solution of claim 11 further comprising a wetting agent selected from the group consisting of a polysorbate surfactant, a polyoxyethylene surfactant, a phosphonates, a saponin, a polyethyoxylated glyceride, and a polyethoxylated castor oil.

15. The contact lens solution of claim 11 further comprising a polyethoxylated castor oil.

16. The contact lens solution of claim 11, further comprising between 0.01% and 5.0% of at least one simple saccharide selected from the group consisting of mannitol; sorbitol; sucrose; dextrose, glycerin and combinations thereof.

17. The contact lens solution of claim 11, further comprising between 0.001% and 1% of a chelating agent selected from the group consisting of ethylenediaminetetraacetic acid or a salt thereof, citric acid or a salt thereof, an amino carboxylic acid or a salt thereof, nitrilotriacetic acid or a salt thereof, diethylene triamine pentaacetic acid or a salt thereof, hydroxyethylethylenediaminetriacetic acid or a salt thereof, 1,2-diaminocyclohexanetetraacetic acid or a salt thereof, ethylene glycol bis (beta-aminoethyl ether)-N,N,N', N' tetraacetic acid (EGTA) or a salt thereof, iminodiacetic acid or a salt thereof, hydroxyethylamino diacetic acid or a salt thereof and a polyphosphate salt.

18. The contact lens solution of claim 11, further comprising between 0.001% and 1% of ethylenediaminetetraacetic acid or a salt thereof.

19. The contact lens solution of claim 11, further comprising between 0.00001% and 0.1% of a microbicide selected from the group consisting of N-alkyl-2-pyrrolidone, chlorhexidine, polyhexamethylene biguanide, hexetidine, bronopol, alexidine, hydrogen peroxide, and salts thereof.

20. The contact lens solution of claim 11, wherein the panthenol is pantothenic acid (B5) or a salt of pantothenic acid.

* * * * *